(12) United States Patent
DeToro et al.

(10) Patent No.: US 6,793,638 B1
(45) Date of Patent: Sep. 21, 2004

(54) LEG STABILIZATION AND ALIGNMENT DEVICE

(75) Inventors: William DeToro, Poland, OH (US); Brian Perala, Geneva, OH (US)

(73) Assignee: Anatomical Concepts, Inc., Boardman, OH (US)

( * ) Notice: Subject to any disclaimer, the term of this patent is extended or adjusted under 35 U.S.C. 154(b) by 0 days.

(21) Appl. No.: 10/265,492

(22) Filed: Oct. 7, 2002

(51) Int. Cl.[7] .................................................. A61F 5/00
(52) U.S. Cl. ............................ 602/23; 128/882; 602/27
(58) Field of Search .............................. 602/23, 26, 27, 602/60, 65; 128/882

(56) References Cited

U.S. PATENT DOCUMENTS

| | | | |
|---|---|---|---|
| 5,088,479 A | * | 2/1992 | Detoro ........................ 602/27 |
| 5,197,942 A | | 3/1993 | Brady |
| 5,421,822 A | * | 6/1995 | Wang .......................... 602/27 |
| 5,545,127 A | * | 8/1996 | Detoro ........................ 602/27 |
| 5,843,010 A | | 12/1998 | Bodmer |
| 5,897,520 A | | 4/1999 | Gerig |
| 6,053,884 A | * | 4/2000 | Peters ......................... 602/16 |
| 6,056,713 A | | 5/2000 | Hayashi |
| 6,102,881 A | * | 8/2000 | Quackenbush ............... 602/27 |
| 6,302,858 B1 | | 10/2001 | DeToro et al. |

* cited by examiner

*Primary Examiner*—Michael A. Brown

(57) ABSTRACT

A leg restraint and alignment device for use with ankle and foot orthotic braces used in support and immobilization of a patient's ankle and foot. The device is of a contoured L-shaped configuration with a curved leg engagement portion extending from a bifurcated attachment portion. A leg pad is removably attached to the leg portion with an adjustable fabric strap fastener extending in oppositely disposed relation thereto about the patient's leg.

8 Claims, 4 Drawing Sheets

LEG STABILIZATION AND ALIGNMENT DEVICE

BACKGROUND OF THE INVENTION

1. Technical Field

This invention relates to therapeutic leg and foot braces and more particularly to leg stabilization and alignment apparatus that are used in connection with such braces.

2. Description of Prior Art

Orthotic foot and ankle braces are used for immobilizing and stabilization of the leg, ankle and foot. Individuals that suffer with a "Varus" condition which is the turning in of the foot so that the patient walks on the side of the foot have special need for leg stabilization. It has been determined that by applying corrective pressure at specific points will stabilize the subtalar which will prevent calcaneal varus. Such orthotic leg and foot braces typically have prefabricated foot and leg engagement portion with multiple soft flexible fastening or support straps. Given the nature of such attachment straps they are not capable of restricting the translateral mount of the leg and ankle indicated in the Varus condition, as noted. By providing an adjustable rigid contoured extension from the leg engagement portion of the brace, leg movement is restricted assisting in the stable lateral alignment of the leg and foot heretofore not available in such brace configurations.

Prior art devices do not address this problem in combination with an ankle and foot orthosis brace, see for example U.S. Pat. Nos. 5,197,942, 5,843,010, 5,897,520, 6,056,713 and applicant's own U.S. Pat. No. 6,302,858.

In U.S. Pat. No. 5,197,942, a customized foot orthosis is disclosed having a back portion and a front portion secured continuously on the foot, ankle and lower leg portion of the patient.

U.S. Pat. No. 5,843,010 is directed to a heel and ankle appliance in which multiple support straps provide in combination an ankle and foot leg support.

U.S. Pat. No. 5,897,520 claims a unitary dorsal night splint in which a rigid upright member is secured around the patient's ankle and foot and lower leg portion. Ankle splints extend on each side of the ankle and wrap there around.

A moldable custom fitted ankle brace is set forth in U.S. Pat. No. 6,056,713 in which moldable thermoplastic is shaped around the foot and ankle of the patient. Fastening straps extend about the brace elements and the ankle and the foot holding the brace in place.

Applicant's U.S. Pat. No. 6,302,858 illustrates a compound adjustable ankle and foot orthosis brace which provides a contoured leg support portion adjustably interconnected to a foot enclosure and walking pad.

SUMMARY OF THE INVENTION

A leg restraint and alignment device for use on a foot and ankle brace to restrict leg and ankle from transverse deflection which causes the foot to turn in and rotate during walking. The leg restraint and alignment device comprises an armature that is selectively secured on the leg portion of the orthotic brace. A contoured portion of the armature extends outwardly along one side of the brace which is secured to the leg portion of the brace. The leg restraint and alignment device is removably adapted to be inverted and secured to the opposite side of the leg portion so as to engage the opposite side of the leg within the leg brace preventing the foot from axial rotation during walking.

DESCRIPTION OF THE PREFERRED EMBODIMENT

Figure 1:
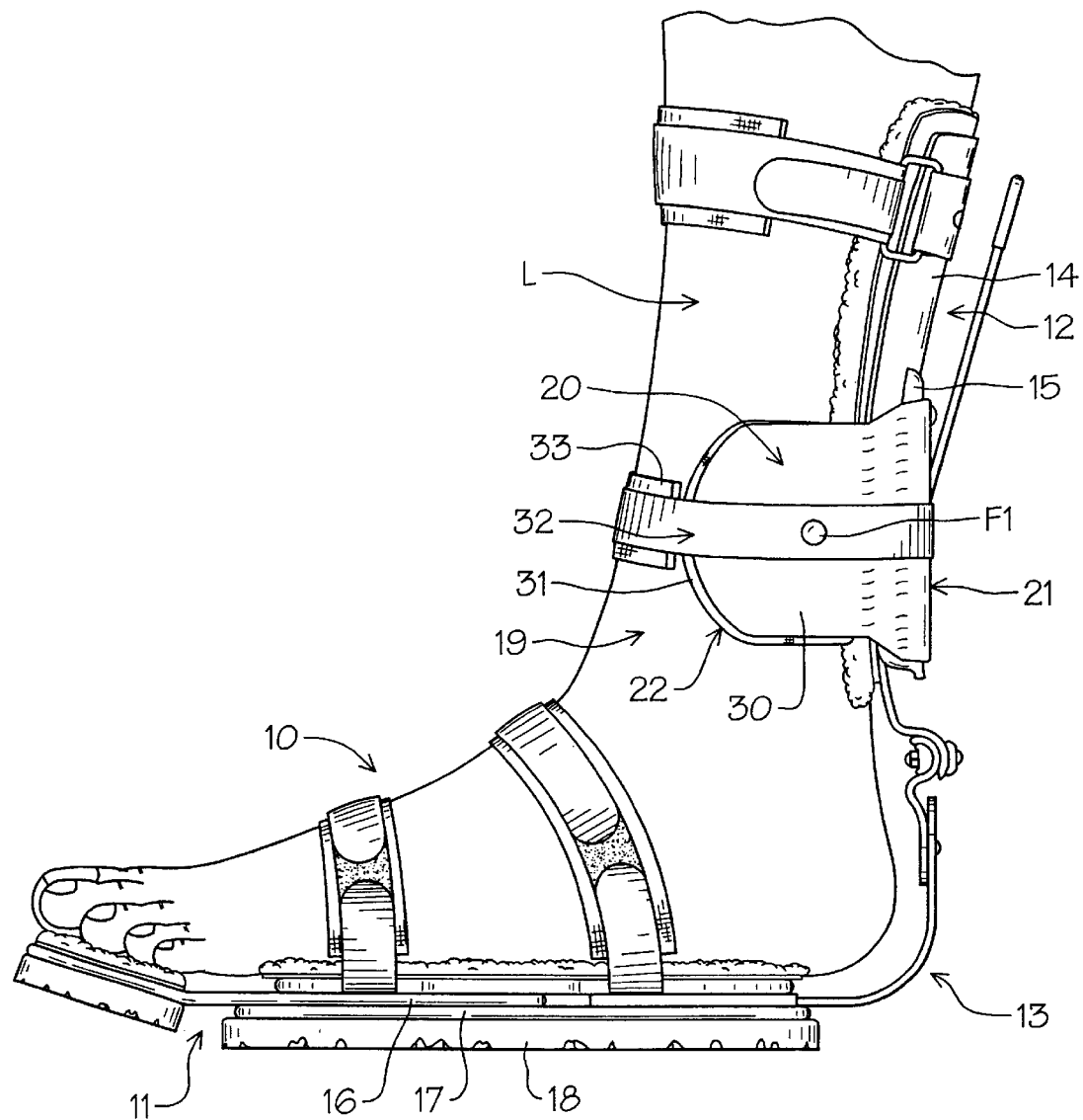
FIG. 1 is a side elevational view of the present invention positioned on a brace.
Figure 2:
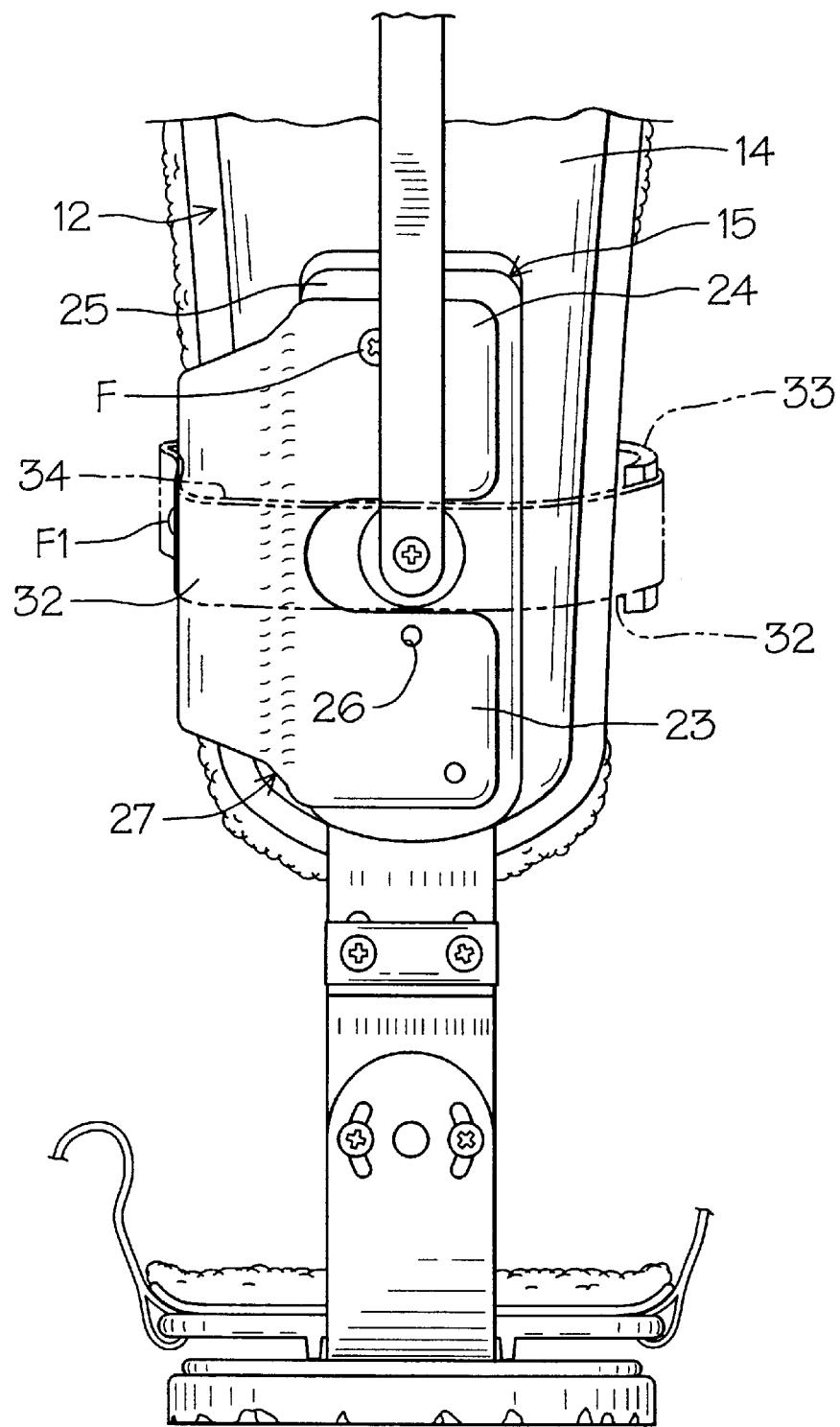
FIG. 2 is a partial rear elevational view thereof.
Figure 3:
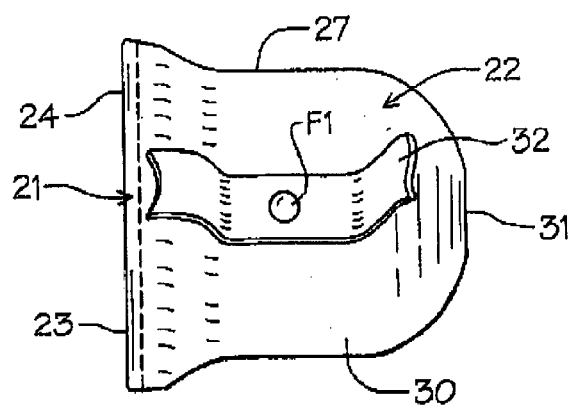
FIG. 3 is a side elevational view of the invention.
Figure 6:
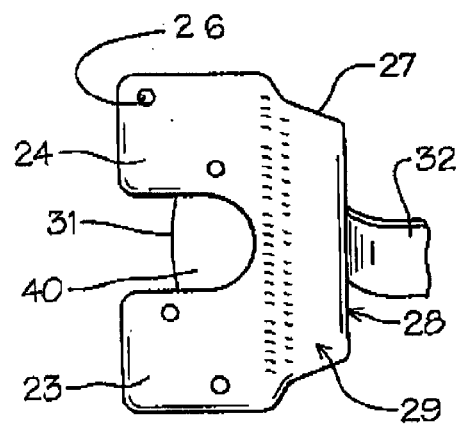
FIG. 6 is a rear elevational view of the invention with portions broken away.

Referring to FIGS. 1 and 2 of the drawings, an ankle and foot orthosis brace 10 can be seen having a foot portion 11, a leg portion 12 and an interconnecting heel portion 13 extending there between. The leg portion 12 has an enlarged transversely contoured leg support 14 portion with a recessed channel 15 formed therein. The foot portion 11 has a footpad 16 attached to an attachment brace element 17. A resilient walking pad 18 is secured to the attachment brace element 17.

A leg restraint and alignment device 19 of the invention is secured to the hereinbefore-described leg portion 12 and extends partially there around and outwardly there from as best seen in FIG. 1 of the drawings. The leg restraint and alignment device 19 has a main body member 20 with a mounting portion 21 and a contoured leg engagement portion 22 extending there from. The mounting portion 21 is bifurcated defining a pair of apertured attachment tabs 23 and 24. The tabs 23 and 24 are in spaced vertical planar relation to one another so as to be engageable on an exterior surface 25 of the recessed channel 15 of the leg support 14 portion as best seen in FIGS. 1–5 of the drawings.

The tabs 23 and 24 are aligned on the surface 25 of the recessed channel 15 so that fasteners F can be threadably disposed within threaded apertures 26 formed within as will be well understood by those skilled in the art.

Figure 4:
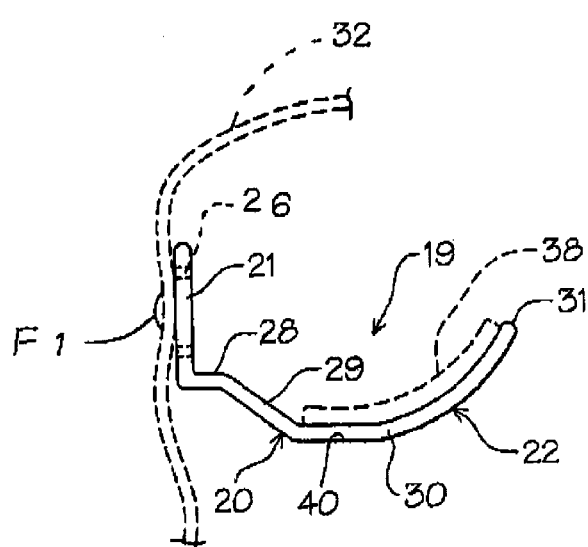
FIG. 4 is a top plan view of the invention with portions broken away.
Figure 5:
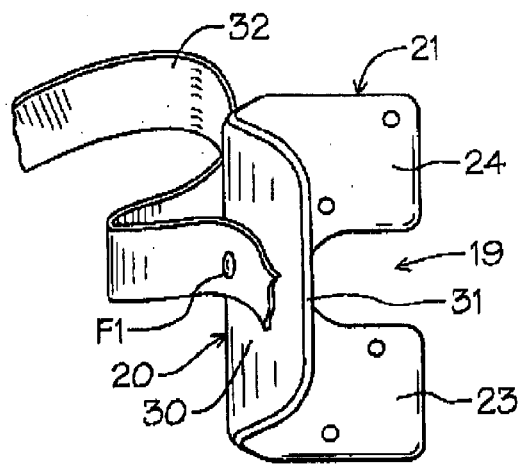
FIG. 5 is an opposite side elevational view of the invention with portions broken away.

The leg engagement portion 22 of the main body member 20 is of a reduced transverse dimension at 27 to that of the mounting portion 21 and extends initially at 90 degrees thereto at 28 as best seen in FIG. 4 of the drawings. An angularly offset transition portion 29 extends there from to a contoured portion 30 adjacent a portion of the patient's leg L as seen in FIG. 1 of the drawings. The contoured portion 30 has an arcuate edge configuration at 31 with a moderate return partially overlying a portion of the mounting portion 21 in spaced relation thereto.

Referring now to FIGS. 1, 3, 5 and 7 of the drawings, a leg engagement strap 32 can be seen secured to the leg engagement portion 22 by a single fastener F1. The strap 32 has a leg pad 33 extending along a portion of its inner surface 34 in longitudinally spaced relation to the fastener F1. A strip of "hook type" material 34A that of hook and loop fasteners known in the art is affixed to the strap 32's outer surface 35 opposite the hereinbefore described leg pad 33 as illustrated most clearly in FIG. 7 of the drawings.

A remaining portion 36 of the strap 32 extending from the fastener F1 and conversely has a "loop type" material 34B of the aforementioned hook and loop material commercially known as Velcro along its inner surface 37. This arrangement of hook and loop material on the strap 32 will allow for selective adjustable size by overlapping engagement around the front of the patient's leg 31.

In use, a secondary pad 38 is removably secured to an inner leg effacing surface 40 of the contoured mounting portion 21 shown in broken lines in FIG. 4 of the drawings. Once engaged on the leg L, the leg restraint and alignment device 19 will retain and restrain the leg from trans-lateral displacement during use implicit of a "Varus" condition in which the patient's foot F turns, thus walking on the side edge of the foot 38.

Figure 7:
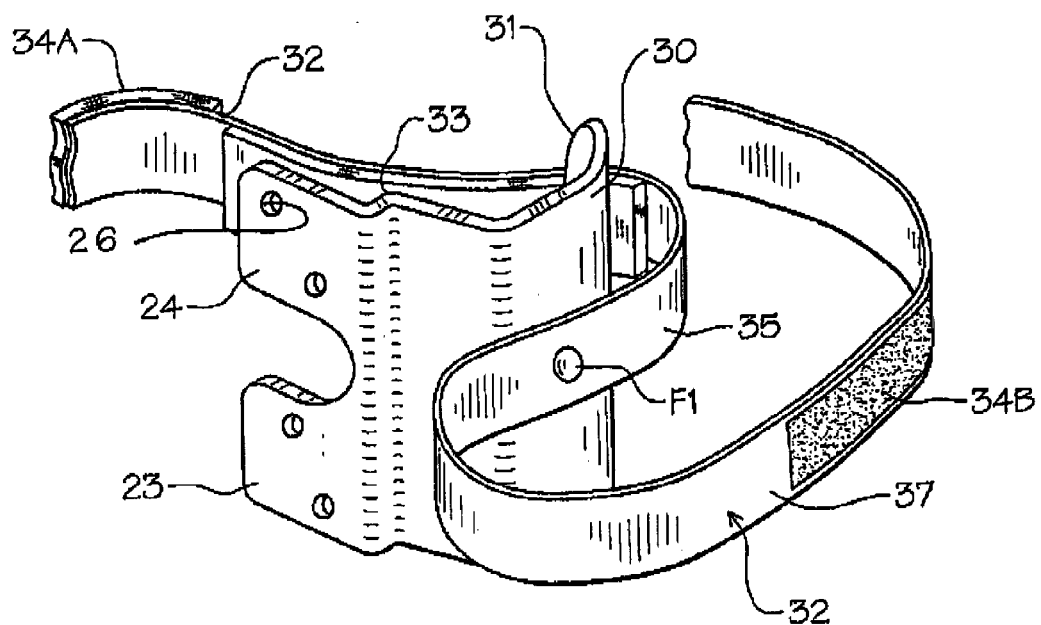
FIG. 7 is a perspective view of the invention with portions broken away.

The leg restraint and alignment device 19 stabilizes lateral movement of the leg L and foot F and be selectively repositioned on the leg engagement portion 22 of the brace 10 on opposite sides thereof by simply removing fasteners F from the aperture 26 and inverting the restraint and alignment device 19 as illustrated figure 7 of the drawings and re-attaching to the leg support 14 portion opposite to the orientation illustrated in FIGS. 1 and 2 of the drawings.

It will thus be seen that a new and novel leg restraint and alignment device for use on orthotic ankle and foot braces has been illustrated and described and that various changes and modifications may be made thereto without departing from the spirit of the invention.

Therefore We claim:

1. A leg restraint and alignment device for use on an orthotic ankle and foot brace comprises in combination,
    a monolithic contoured body member secured to a leg portion of an ankle and foot brace,
    said body member having a mounting portion and a leg engagement portion,
    said mounting portion engageable on said leg of the ankle and foot brace portion,
    said leg engagement portion has an arcuate contoured portion, in angularly offset relation to said mounting portion,
    means for selectively reversing orientation attachment of said body member with said leg portion, a flexible retaining strap secured to said body member,
    means for adjustably securing said respective ends of said retaining strap to one another.

2. The leg restraint and alignment device set forth in claim 1 wherein said mounting portion is bifurcated defining spaced aperture tabs.

3. The leg restraint and alignment device set forth in claim 1 wherein said means for selectively reversing orientation attachment of said mounting portion of said body member with said leg portion comprises,
    diagonally aligned apertures in each of mounting tabs and at least one aperture in each tab in vertical alignment with one another, fasteners extending through said respective apertures threadably engageable with said leg portion of said ankle and foot brace.

4. The leg restraint and alignment device set forth in claim 1 wherein said means for adjustably securing the ends of said retaining strap to one another comprises,
    hook and loop material on respective inner and outer surfaces of said strap adjacent ends.

5. The leg restraint and alignment device set forth in claim 4 wherein one of said retaining strap ends has an elongated pad on its inner surface opposite said hook material thereon.

6. The leg restraint and alignment device set forth in claim 1 wherein said leg engagement portion of said body member is of a reduced transverse dimension to that of said mounting portion of said body member.

7. The leg restraint and alignment device set forth in claim 1 wherein said leg engagement portion of said body member has a leg engagement pad on an inner surface of said arcuate contoured portion.

8. The leg restraint and alignment device set forth in claim 1 wherein said retaining strap is secured to said outer surface of said arcuate contoured portion.

\* \* \* \* \*